US012778896B2

(12) United States Patent
Xiao et al.

(10) Patent No.: US 12,778,896 B2
(45) Date of Patent: Nov. 3, 2026

(54) METHOD FOR TREATING CANCER WITH AN ORAL DOSAGE FORM OF AN FGFR4 INHIBITOR

(71) Applicant: Eisai R&D Management Co., Ltd., Tokyo (JP)

(72) Inventors: Jianjun Xiao, Lexington, MA (US); Nathalie M. Rioux, Woburn, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 647 days.

(21) Appl. No.: 17/998,398

(22) PCT Filed: May 14, 2021

(86) PCT No.: PCT/US2021/032552
§ 371 (c)(1),
(2) Date: Nov. 10, 2022

(87) PCT Pub. No.: WO2021/231928
PCT Pub. Date: Nov. 18, 2021

(65) Prior Publication Data

US 2023/0172867 A1 Jun. 8, 2023

Related U.S. Application Data

(60) Provisional application No. 63/025,924, filed on May 15, 2020.

(51) Int. Cl.

| | |
|---|---|
| ***A61K 9/48*** | (2006.01) |
| ***A61K 31/506*** | (2006.01) |
| ***A61P 1/16*** | (2006.01) |
| ***A61P 35/00*** | (2006.01) |

(52) U.S. Cl.
CPC .......... *A61K 9/4866* (2013.01); *A61K 9/4858* (2013.01); *A61K 31/506* (2013.01); *A61P 1/16* (2018.01); *A61P 35/00* (2018.01)

(58) Field of Classification Search
CPC .. A61K 9/4866; A61K 9/4858; A61K 31/506; A61P 1/16; A61P 35/00; A61P 43/00
See application file for complete search history.

(56) References Cited

U.S. PATENT DOCUMENTS

| | | | |
|---|---|---|---|
| 9,434,697 B2 | 9/2016 | Reynolds et al. | |
| 10,562,888 B2 | 2/2020 | Moniz et al. | |
| 2009/0048175 A1* | 2/2009 | Shailubhai | A61K 9/02 530/326 |
| 2011/0104288 A1 | 5/2011 | Thoorens et al. | |
| 2011/0171201 A1* | 7/2011 | Siegel | A61P 1/04 424/94.63 |
| 2015/0118299 A1 | 4/2015 | Ueki | |
| 2016/0193151 A1 | 7/2016 | Noriega Escobar et al. | |
| 2018/0093972 A1 | 4/2018 | Moniz et al. | |
| 2019/0117640 A1 | 4/2019 | Selvaraj et al. | |
| 2019/0175598 A1 | 6/2019 | Selvaraj et al. | |
| 2020/0206222 A1 | 7/2020 | Reynolds et al. | |
| 2020/0317645 A1 | 10/2020 | Moniz et al. | |

FOREIGN PATENT DOCUMENTS

| | | |
|---|---|---|
| JP | 2013510157 A | 3/2013 |
| JP | 2016-535000 A | 11/2016 |
| JP | 2018-511635 A | 4/2018 |
| JP | 2019-515010 A | 6/2019 |
| JP | 2019-528302 A | 10/2019 |
| WO | 2012001977 A1 | 1/2012 |
| WO | 2015030021 A1 | 3/2015 |
| WO | 2016168331 A1 | 10/2016 |
| WO | 2019/139977 A1 | 7/2019 |

OTHER PUBLICATIONS https://www.cdc.gov/nchs/fastats/body-measurements.htm referenced on Mar. 21, 2025.*
Office Action (Notice of Reasons for Rejection) issued on May 7, 2024, by the Japanese Patent Office in Japanese Patent Application No. 2022-569143, and an English Translation of the Office Action. (6 pages).
Rioux, N. et al."Effect of a high-fat meal on the relative bioavailability of H3B-6527, a novel FGFR4 inhibitor, in healthy volunteers" Cancer Chemother Pharmacol., Oct. 27, 2018, vol. 83, No. 1, pp. 91-96.
Joshi, J. J. et al."H3B-6527 Is a Potent and Selective Inhibitor of FGFR4 in FGF19-Driven Hepatocellular Carcinoma" Cancer Research, Dec. 15, 2017, vol. 77, No. 24, pp. 6999-7013.
International Search Report (PCT/ISA/210) and Written Opinion (PCT/ISA/237) mailed on Aug. 25, 2021, by the European Patent Office as the International Searching Authority for International Application No. PCT/US2021/032552.
ASCO Meeting Library, "A Phase I Study of H3B-6527 in Hepatocellular Carcinoma (HCC) or Intrahepatic Cholangiocarcinoma (ICC) Patients (pts)", Teresa Maraculla Mercade et al., online Jun. 3, 2019. (2 pages).
ASCO 2019 Poster Abstract 4095, Jun. 3, 2019, "A Phase 1 Study of H3B-6527 in Hepatocellular Carcinoma or Intrahepatic Cholangiocarcinoma Patients", Teresa Macarulla, MD, PhD et al.
Gastrointestinal (Noncolorectal) Cancer, Abstract 4085, Poster Session (Board #200), May 15, 2019, Mon, 8:00 AM-11:00 Am, "A Phase I Study of H3B-6527 in Hepatocellular Carcinoma (HCC) or Intrahepatic Cholangiocarcinoma (ICC) Patients (pts)", Teresa Maraculla Mercade.
Office Action (Notice of Reasons for Rejection) issued on Apr. 7, 2026 in Japanese office Action No. 2025-037115, 6 pages.

* cited by examiner

*Primary Examiner* — Jessica Worsham
(74) *Attorney, Agent, or Firm* — Buchanan Ingersoll & Rooney PC

(57) ABSTRACT

The present invention relates to pharmaceutical compositions comprising an inhibitor of FGFR4, and methods of cancer therapy using the FGFR4 inhibitor. In particular, described herein are dosages of H3B-6527 with defined pharmacokinetic (PK) profiles that allow the inhibitor to be efficaciously and safely administered to a human subject in need thereof.

29 Claims, 4 Drawing Sheets

METHOD FOR TREATING CANCER WITH AN ORAL DOSAGE FORM OF AN FGFR4 INHIBITOR

CROSS-REFERENCE TO RELATED APPLICATIONS

This application claims the benefit of U.S. Provisional Patent Application No. 63/025,924, filed on May 15, 2020. That application is incorporated by reference as if fully rewritten herein.

BACKGROUND OF THE INVENTION

It has been shown that alterations in fibroblast growth factor receptor (FGFR) signaling correlate with outcomes of hepatocellular carcinoma (HCC) and intrahepatic cholangiocarcinoma (ICC) patients. Cheng A L. *Eur J Cancer.* 2012; 48 (10): 1452-1465; and Yoo C. *Oncotarget.* 2017; 8 (24): 38592-38601. Fibroblast growth factor 19 (FGF19) is a protein hormone secreted by the gut which acts in the liver through FGFR4 to regulate bile acid synthesis. FGFR4 is the major receptor for FGF19 and is highly expressed in liver. Genomic studies in humans and functional studies in mice have implicated FGF19 as an oncogene in HCC and ICC. Sawey E T. *Cancer Cell.* 2011; 19 (3): 347-358; and Sia D. *Gastroenterology.* 2013; 144 (4): 829-840. Genomic studies showed that a subset of HCC (~30%) overexpress FGF19, and this overexpression is hypothesized to hyperactivate FGFR4 and its downstream signaling pathway leading to enhanced tumor growth in HCC/ICC. Targeting FGFR4 may have therapeutic benefits in HCC/ICC with altered FGF19 signaling. Targeting FGFR4 may have therapeutic benefits in sarcoma, particularly rhabdomyosarcoma, with altered FGF19 signaling.

Recently, the compound of Formula I has been discovered and identified to be a potent and selective inhibitor of FGFR4:

(Formula I)

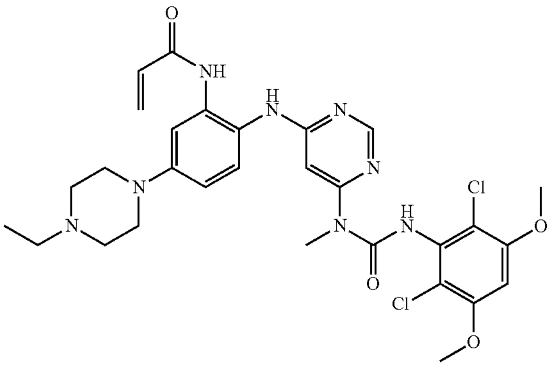

N-(2-((6-(3-(2,6-dichloro-3,5-dimethoxyphenyl)-1-methylureido)pyrimidin-4-yl)amino)-5-(4-ethylpiperazin-1-yl)phenyl)acrylamide This compound has been described in U.S. Pat. No. 9,434,697. Its various crystalline forms has been described in published US patent application publication no. 2018/0093972.

Though Formula I has been shown to be effective in in vitro and in vivo models, the manner by which Formula I should be administered to human cancer patient in need of treatment has yet to be determined. Hence, there is a need to devise a formulation and dosage regimen of H3B-6527 that will allow the inhibitor to be more efficaciously and safely administered to a human subject in need thereof so the pharmacokinetic (hereinafter PK) profile of Formula I can be determined. Once the PK profile of Formula I has been deduced, a therapeutic dose or amount of Formula I can be determined and employed in cancer treatment methods. Identifying the PK profile that correlates with HCC and sarcoma patient efficacy and safety affords its general use in human treatment methods for these cancers.

BRIEF SUMMARY

Embodiments may provide an oral dosage form comprising a compound given by Formula I or a pharmaceutically acceptable salt thereof, and at least one pharmaceutically acceptable excipient, wherein said compound of Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure (Formula I)

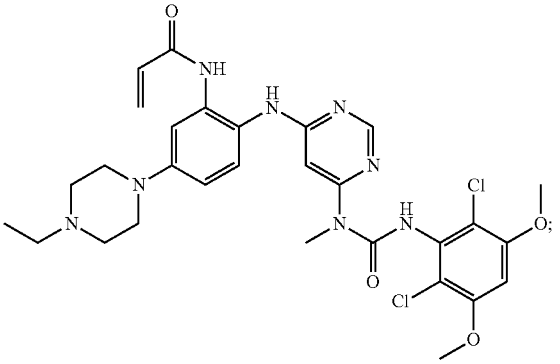

and wherein said oral dosage form when administered orally to a human subject is formulated to achieve a mean $C_{max}$ of Formula I of about 10 ng/mL to about 1000 ng/ml. In further embodiments the mean $C_{max}$ of Formula I is about 100 ng/ml to about 400 ng/ml. In further embodiments said mean $C_{max}$ of Formula I is about 100 ng/ml to about 300 ng/ml. In further embodiments said mean $C_{max}$ of Formula I is in the range of 80% to 125% of 100 ng/ml to 80% to 125% of 400 ng/mL. In further embodiments the dosage form is formulated to achieve a mean $t_{max}$ of said mean $C_{max}$ in about 0.5 hours to about 8 hours. In further embodiments the dosage form is formulated to achieve a mean $t_{max}$ of said mean $C_{max}$ in about 2 hours to about 6 hours after administration of said dosage form to said a human subject. In further embodiments the dosage form is formulated to achieve a mean $t_{max}$ of said mean $C_{max}$ in about 2 hours to about 4 hours after administration of said dosage form to said a human subject. In further embodiments the dosage form is formulated to achieve a mean $t_{max}$ of said mean $C_{max}$ in about 2 hours to about 3 hours after administration of said dosage form to said a human subject. In further embodiments the dosage form comprises a total equivalent of about 300 mg to about 2000 mg of Formula I. In further embodiments the dosage form comprises a total equivalent of about 500 to about 1400 mg of Formula I.

Further embodiments provide an oral dosage form comprising a compound given by Formula I or a pharmaceutically acceptable salt thereof and at least one pharmaceutically acceptable excipient, wherein said Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

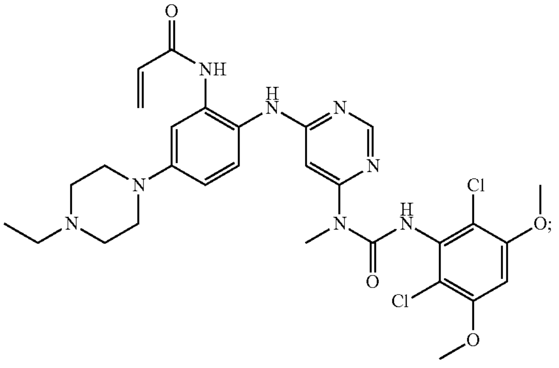

and wherein said oral dosage form when administered orally to a human subject is formulated to achieve a mean $AUC_{0-24}$ of Formula I of about 50 h*ng/ml to about 5700 h*ng/ml. In further embodiments said mean $AUC_{0-24}$ is about 100 h*ng/ml to about 1200 h*ng/ml. In further embodiments said mean $AUC_{0-24}$ is in the range of 80% to 125% of 100 h*ng/ml to 80% to 125% of 1200 h*ng/mL. In further embodiments said dosage form comprises a total equivalent of about 300 mg to about 2000 mg of Formula I. In further embodiments said dosage form comprises a total equivalent of about 600 mg to about 1000 mg of Formula I.

Further embodiments provide an oral dosage form for administration to a human subject comprising a compound given by Formula I or a pharmaceutically acceptable salt thereof, and at least one pharmaceutically acceptable excipient, wherein said compound of Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

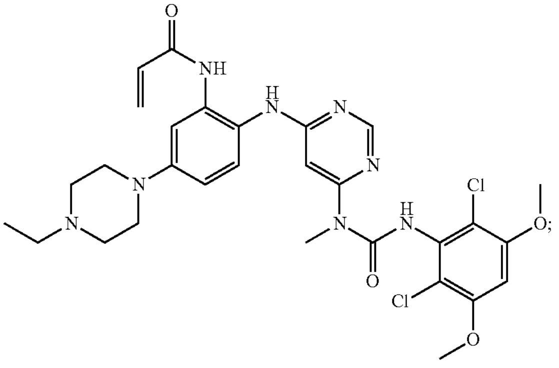

and wherein said oral dosage form when administered orally to a human subject is formulated to achieve a mean $t_{1/2}$ of Formula I of said dosage of about 1 hour to about 6 hours. In a further embodiment said mean $t_{1/2}$ is about 1 hour to about 5 hours. In further embodiments said mean $t_{1/2}$ is about 2 hours to about 3 hours. In further embodiments the dosage form comprises a total equivalent of about 300 mg to about 2000 mg of Formula I. In still further embodiments the dosage form comprises a total equivalent of about 500 mg to about 1000 mg of Formula I.

Further embodiments provide an oral dosage form comprising a compound given by Formula I or a pharmaceutically acceptable salt thereof, and at least one pharmaceutically acceptable excipient, wherein said compound of Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

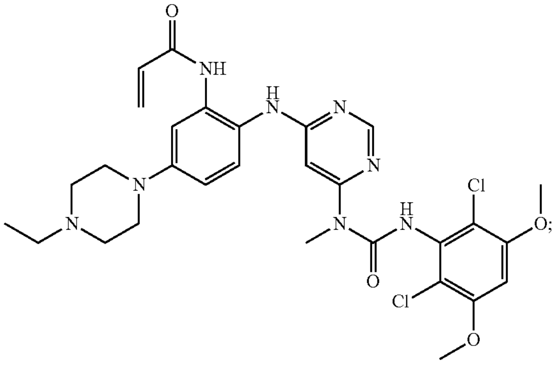

and wherein said oral dosage form when administered orally to a human subject is formulated to achieve a mean $AUC_{0-12}$ of Formula I of about 400 h*ng/mL to about 1200 h*ng/mL. In some embodiments in said mean $AUC_{0-12}$ is about 400 h*ng/mL to about 700 h*ng/ml. In some embodiments the mean $AUC_{0-12}$ is in the range of 80% to 125% of 400 h*ng/mL to 80% to 125% of 1200 h*ng/mL. In some embodiments as reported above the dosage form comprises a total equivalent of about 500 mg to about 700 mg of Formula I.

Another embodiment includes a dosage form as described herein having means to achieve the pharmacokinetic values described herein.

In some embodiments an oral dosage form is a capsule comprising an internal phase comprising Formula I or a pharmaceutically acceptable salt, lactose monohydrate, calcium carbonate, copovidone, low-substituted hydroxypropyl cellulose, colloidal silicon dioxide, and magnesium stearate. In some embodiments the capsule further comprises an external phase comprising magnesium stearate. In some embodiments the internal phase is contained within a hypromellose capsule. Some embodiments comprise the free-base form of Formula I.

A further embodiment provides a method of treating cancer in a human subject comprising administering to said subject an oral dosage form comprising a therapeutically effective amount of a compound given by Formula I or a pharmaceutically acceptable salt thereof, and at least one pharmaceutically acceptable excipient, wherein said Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

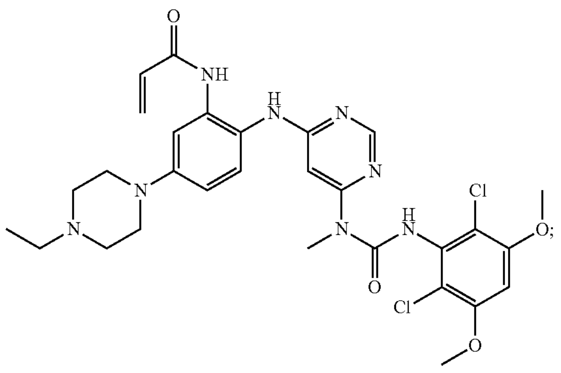

wherein said therapeutically effective amount is a dose ranging from about 300 mg to about 2000 mg of Formula I; and, wherein said oral dosage form has a mean $C_{max}$ of Formula I of about 10 ng/ml to about 1000 ng/mL. In some embodiments the mean $C_{max}$ of Formula I is about 100 ng/ml to about 400 ng/mL. In some embodiments the mean $C_{max}$ of Formula I is about 100 ng/ml to about 300 ng/mL. In some embodiments the mean $C_{max}$ of Formula I is in the range of 80% to 125% of 100 ng/mL to 80% to 125% of 400 ng/mL. In some embodiments the dosage form has a mean $t_{max}$ of said mean $C_{max}$ of Formula I of about 0.5 hours to about 8 hours. In some embodiments the dosage form has a mean $t_{max}$ of said mean $C_{max}$ of about 2 hours to about 6 hours. In some embodiments the dosage form has a mean $t_{max}$ of said mean $C_{max}$ of about 2 hours to about 4 hours. In some embodiments the dosage form has a mean $t_{max}$ of said mean $C_{max}$ of about 2 hours to about 3 hours. In further embodiments the dosage form comprises a total equivalent of about 500 mg to about 1000 mg of Formula I. In further embodiments the dosage form comprises a total equivalent of about 1000 to about 1400 mg of Formula I.

Further embodiments provide a method of treating cancer in a human subject comprising administering to said subject once daily an oral dosage form comprising a therapeutically effective amount of a compound given by Formula I or a pharmaceutically acceptable salt thereof, and at least one pharmaceutically acceptable excipient, wherein said Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

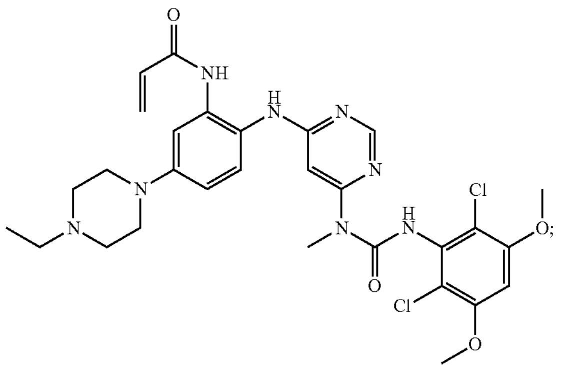

wherein said therapeutically effective amount is a dose ranging from about 300 mg to about 2000 mg of Formula I; and, wherein said oral dosage form has a mean $AUC_{0-24}$ of Formula I of about 50 h*ng/ml to about 5700 h*ng/mL. In further embodiments said mean $AUC_{0-24}$ is about 100 h*ng/ml to about 1200 h*ng/mL. In further embodiments said mean $AUC_{0-24}$ is in the range of 80% to 125% of 100 h*ng/ml to 80% to 125% of 1200 h*ng/mL. In further embodiments the dosage form comprises a total equivalent of about 500 mg to about 1000 mg of Formula I. In still further embodiments the dosage form comprises a total equivalent of about 1000 mg to about 1400 mg of Formula I.

A further embodiment provides method of treating cancer in a human subject comprising administering to said subject an oral dosage form comprising a therapeutically effective amount of a compound given by Formula I or a pharmaceutically acceptable salt thereof, and at least one pharmaceutically acceptable excipient, wherein said Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

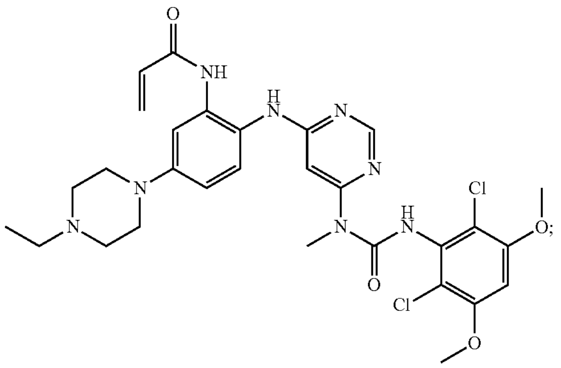

wherein said therapeutically effective amount is a dose ranging from about 300 mg to about 2000 mg of Formula I; and, wherein said oral dosage form has a mean $t_{1/2}$ of Formula I of said dosage form of about 1 hour to about 6 hours. In a further embodiment said mean $t_{1/2}$ is about 1 hour to about 5 hours. In a still further embodiment said mean $t_{1/2}$ is about 2 hours to about 3 hours. In a further embodiment the dosage form comprises a total equivalent of about 500 mg to about 1000 mg of Formula I. In a still further embodiment the dosage form comprises a total equivalent of about 1000 mg to about 1400 mg of Formula I.

A further embodiment provides a method of treating cancer in a human subject comprising administering to said subject twice daily an oral dosage form comprising a therapeutically effective amount of a compound given by Formula I or a pharmaceutically acceptable salt thereof, and at least one pharmaceutically acceptable excipient, wherein said Formula I is N-(2-((6-(3-(2,6-dichloro-3,5-dimethoxyphenyl)-1-methylureido)pyrimidin-4-yl)amino)-5-(4-ethylpiperazin-1-yl)phenyl)acrylamide represented by the structure:

(Formula I)

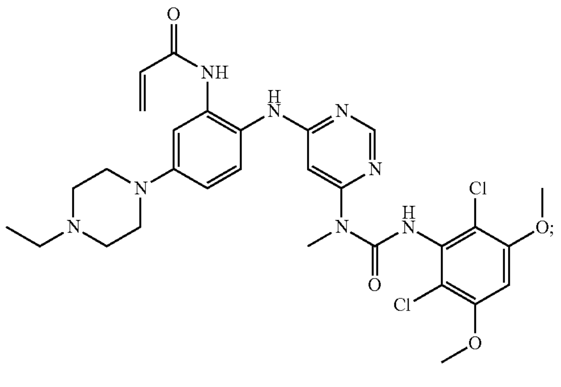

wherein said therapeutically effective amount is a dose ranging from about 500 mg to about 700 mg of Formula I; and, wherein said oral dosage form has a mean $AUC_{0-12}$ of Formula I of about 400 h*ng/ml to about 1200 h*ng/mL. In a further embodiment the said mean $AUC_{0-12}$ is about 400 h*ng/ml to about 700 h*ng/ml. In a further embodiment the mean $AUC_{0-12}$ is in the range of 80% to 125% of 400 h*ng/ml to 80% to 125% of 1200 h*ng/mL.

In further embodiments of the methods reported herein the oral dosage form is a capsule comprising an internal phase comprising Formula I or a pharmaceutically acceptable salt, lactose monohydrate, calcium carbonate, copovidone, low-substituted hydroxypropyl cellulose, colloidal silicon dioxide, and magnesium stearate. In a further embodiment said capsule further comprises an external phase comprising magnesium stearate. In a further embodiment said internal phase is contained within a hypromellose capsule. In a further embodiment the capsule includes the free-base form of Formula I. In a further embodiment the cancer is hepatocellular carcinoma. In a further embodiment the cancer is sarcoma. In a further embodiment the cancer is rhabdomyosarcoma. In a further embodiment the cancer expresses or overexpresses FGFR4 or FGF19.

In some embodiments the oral dosage form is administered to the human in a fasted state. In some embodiments the oral dosage form is administered to the human in a fed state.

DETAILED DESCRIPTION OF THE EMBODIMENTS

Definitions

Figure 1:
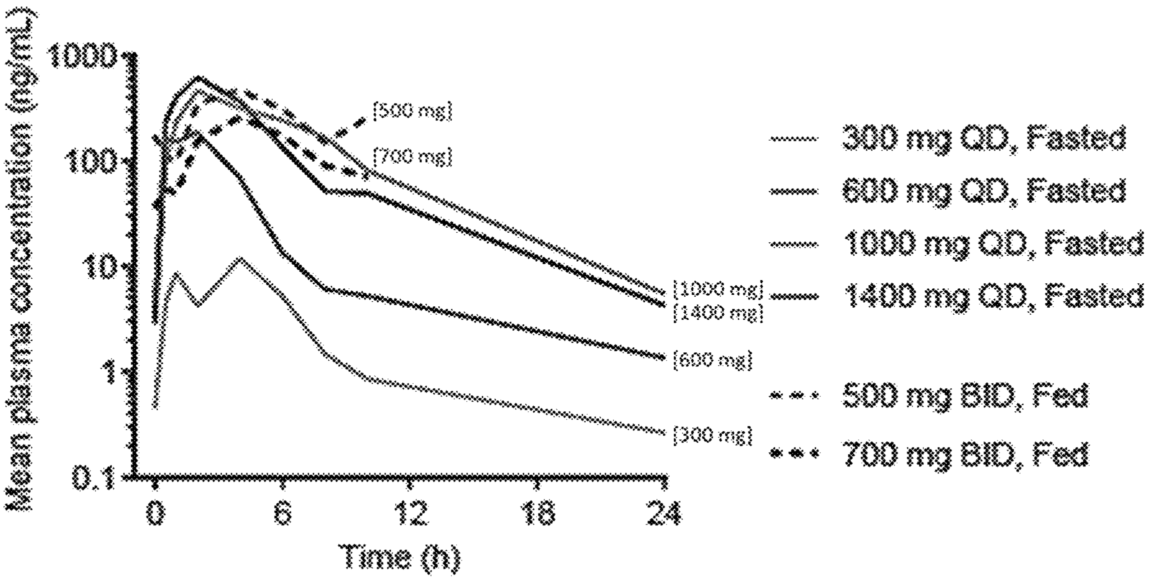
FIG. 1 shows a mean plasma concentration over time profile for H3B-6527 (Cycle 1, Day 8), as further reported in Example 2. Preliminary PK analysis indicates that H3B-6527 plasma exposure increased with dose up to 1000 mg QD in fasted state. A higher minimal plasma concentration was maintained on the BID schedule.

The use of the articles "a," "an," and "the" herein are to be construed to cover both the singular and the plural, unless otherwise indicated herein or clearly contradicted by context. For example, the term "a disintegrant" refers to one or more disintegrants included in or suitable for use in the formulation described herein. Similarly, the term "a therapeutic amount" refers to one or more therapeutic amounts included in or suitable for use in the dosage form.

The terms "comprising," "having," "including," and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The expression "bioequivalent" or "bioequivalence" is a term of art and is intended to be defined in accordance with Approved Drug Products with Therapeutic Equivalence Evaluations, 34th Edition, which is published by the U.S Department of Health and Human Services, and is commonly known as the "Orange Book." Bioequivalence of different formulation of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. Detailed guidelines for establishing the bioequivalence of a formulation with a reference formulation have been published by the FDA Office of Generic Drugs, Division of Bioequivalence.

As used herein, the term "a mean" refers to a geometric mean determined from a collection of independent measurements. For example, the independent measurements may be collected from a statistically meaningful population. As further examples, when used to describe pharmacokinetic parameters (such as "a mean $C_{max}$", "a mean $AUC_{0-x}$", "a mean $AUC_{0-t}$", "a mean $AUC_{0-inf}$", a "mean $t_{max}$", or "a mean $t_{1/2}$" (or "a mean half-life")), "a mean" refers to the geometric mean pharmacokinetic value derived from the population from which individual measurements were respectively collected. Hence, as used herein, a dosage form may be administered to a human subject, wherein the dosage form has a mean pharmacokinetic value derived from a collection of independently measured values.

The list of the abbreviations and definitions of the terms used in this application is as follows. AUC: Area under the plasma concentration-time curve; $AUC_{0-x}$: Area under the plasma concentration-time curve from time zero to x hours after dosing (e.g., x may indicate 12 or 24 hours); $AUC_{0-t}$: Area under the plasma concentration-time curve from time zero to time of last quantifiable concentration; $AUC_{0-inf}$: Area under the plasma concentration-time curve from time zero to infinity; ANCOVA: Analysis of covariance; CI: Confidence interval; $C_{max}$: Maximum drug concentration; $C_x$: plasma concentration at x hours after dosing; CV: Coefficient of variation; LC-MS/MS: Liquid chromatography-mass spectrometry/mass spectrometry; MAD: Multiple ascending dose; MTD: Maximum tolerated dose; PD: Pharmacodynamics; PK: pharmacokinetic(s); RT: Reaction time; SAD: Single ascending dose; SD: Standard deviation; t/2: terminal elimination half-life; $t_{max}$: time to reach maximum (peak) concentration following drug administration. As used herein, $t_{1/2}$ includes the terminal elimination half-life of the drug concentration, which may be the terminal elimination half-life of the $C_{max}$. As used herein, $C_{max}$ includes the maximum drug concentration of a substance as measured in human plasma.

Two dosage forms whose rate and extent of absorption differ by −20%/+25% or less are generally considered "bioequivalent." Another approach for average bioequivalence involves the calculation of a 90% confidence interval for the ratio of the averages (population geometric means) of the measures for the test and reference products. To establish BE, the calculated confidence interval should fall within usually 80-125% for the ratio of the product averages. In addition to this general approach, the others approach, including (1) logarithmic transformation of pharmacokinetic data, (2) methods to evaluate sequence effects and (3) methods to evaluate outlier data, may be useful for the establishment of bioequivalence. For example, in the above (1) the confidence interval should fall within usually 80-125% for the difference in the mean value of the logarithmic converted PK parameter.

The term "about," "approximately," or "approximate," as used herein when referring to a measureable value such as an amount, a temporal duration, and the like, is meant to encompass variations of +20% or 10%, more preferably 5%, even more preferably 1%, and still more preferably 0.1% from the specified value, as such variations are appropriate in the given context.

When a dosage amount or dosage range is mentioned by mass or weight in the format of "Compound of Formula I," or "H3B-6527," or "free base of H3B-6527," a person of skill in the art will appreciate that providing the equivalent molar amount of the active compound as a pharmaceutically acceptable salt will typically require administration of a larger mass of salt than would be required through administration of the compound alone (that is, the amount of free base and amount of salt have a 1:1 molar ratio). For example, the phrase "25 mg to 50 mg of a compound given by Formula I or a pharmaceutically acceptable salt thereof" contemplates the free base of Formula I in amounts from 25 mg to 50 mg (inclusive of endpoints), as well as the monohydrochloride salt of a compound of Formula I in amounts 26 mg to 53 mg (inclusive of endpoints). This conversion may be referred to, for example, as a "salt conversion factor," "salt correction factor," or "potency adjustment factor."

The potency adjustment factor conversion is also applicable to crystalline forms of Formula I existing as a hydrate, solvate, or crystalline forms of Formula I having both i) hydrate or solvate and ii) salt counterions. Moreover, such potency adjustment factor conversions are applicable whether co-crystallized solvent molecules and/or salt counterions exist in the crystalline form in integral or non-integral stoichiometric ratios. Hence, the skilled artisan understands that different potency adjustments may be made for the monohydrochloride salt of H3B-6527, the hemihydrochloride salt of H3B-6527, or other ratios such 1:1.3, 1:1.25, etc.

Consistent with the prior paragraphs above, as used herein, an "equivalent" quantity (e.g., mass, weight, dosage, etc.) of Formula I (or H3B-6527, free base of H3B-6527 or any other of its synonyms as used herein) refers to the quantity of any salt and/or hydrate following its potency adjustment factor.

"H3B-6527 drug substance" refers to a free base of H3B-6527, as reported in U.S. Pat. No. 10,562,888, which is incorporated by reference herein.

As used herein, a "human subject" is interchangeable with a "human subject in need of treatment," or "human subject in need thereof," all of which refer to a human subject having hepatocellular carcinoma or sarcoma, or a human subject having an increased risk of developing hepatocellular carcinoma or sarcoma relative to the population at large. A human subject in need thereof can be one who has been previously diagnosed or identified as having hepatocellular carcinoma or sarcoma or a precancerous condition. Alternatively, a human subject in need thereof can be one who has an increased risk of developing such disorder relative to the population at large (i.e., a subject who is predisposed to developing such disorder relative to the population at large). A human subject in need thereof can have a precancerous condition.

A human subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition.

As used herein, "fasted condition" describes a human subject in need thereof who has undergone an overnight fast of at least 10 hours before administration. No food should be allowed for at least 4 hours post-dose. Water can be allowed as desired except for one hour before and after drug administration.

As used herein, "fed state" describes a human subject who has fasted over 2 hours prior to pharmacodynamics assessments and had a meal prior to or in conjunction with study drug administration.

As used herein, "treating" or "treat" describes the management and care of a human subject for the purpose of combating a disease, condition, or disorder and includes the administration of a dosage form of H3B-6527, or a pharmaceutically acceptable salt, polymorph, hydrate, or solvate thereof, to alleviate the symptoms or complications of a disease, condition or disorder, or to eliminate the disease, condition or disorder.

H3B-6527, or a pharmaceutically acceptable salt and/or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

As used herein, "sample" means any biological sample derived from the human subject which includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, the term "dosage form" refers to physically discrete units suited as unitary dosages for a human subject to be treated; each unit containing a predetermined quantity of active compound calculated to produce the desired therapeutic effect in association with the required pharmaceutical carrier. Dosage forms are classified in terms of administration routes and application sites, including, for example, oral, topical, rectal, vaginal, intravenous, subcutaneous, intramuscular, ophthalmic, nasal, optic and inhalation administration. Alternatively, dosage forms are classified in terms of physical form such as solid, semi-solid or liquid. The dosage form is any of a variety of forms, including, for example, an IV bag, a tablet, a single pump on an aerosol inhaler or a vial. An "oral dosage form" refers to a dosage form that is easily administered to a human subject through the mouth. Non-limiting examples of oral dosage forms include capsules and tablets. The quantity of active ingredient (e.g., a formulation of the disclosed compound or salt, hydrate, or solvate thereof) in a unit dose is an effective amount and is varied according to the particular treatment involved.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient. For example, a pharmaceutically acceptable excipient used for the formulation of the invention can be a diluent or inert carrier, a lubricant, a binder, or a combination thereof. The pharmaceutically acceptable excipient used for the formulation of the invention can further include a filler, an anti-microbial agent, an antioxidant, an anti-caking agent, a coating agent, or a mixture thereof.

The term "composition" as used herein includes a product comprising a particular ingredient in a particular amount and any product directly or indirectly brought about by the combination of particular ingredients in particular amounts. Such a term as it relates to pharmaceutical compositions is intended to include a product comprising an active ingredient (here, Formula I or any of its pharmaceutically acceptable salts, hydrates and/or solvates) and an inert ingredient constituting a carrier and include any product directly or indirectly brought about by the combination, complexation or aggregation of any two or more ingredients or the dissociation, other kinds of reactions or interaction of one or more ingredients. Thus, the pharmaceutical composition of the present invention includes any composition prepared by mixing compounds given by Formula I (or pharmaceutically acceptable salts, hydrates and/or solvates) with a pharmaceutically acceptable excipient.

As used herein, the term "therapeutically effective amount" refers to an amount of H3B-6527 that can produce a therapeutic effect in a human subject. A therapeutically effective amount is an amount that can treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician.

In a preferred aspect, the disease or condition to be treated is cancer. In another aspect, the disease or condition to be treated is a cell proliferative disorder. The therapeutically effective amount of H3B-6527 may be administered in a dosage form. A therapeutically effective amount H3B-6527 may be in the form of a free base, a pharmaceutically acceptable salt, solvate, and/or hydrate.

As used herein, "therapeutic effect" is a consequence of a medical treatment of any kind, the results of which are judged to be desirable and beneficial. This is true whether the result was expected, unexpected, or even an unintended consequence of the treatment. A desirable or beneficial result may be the inhibition of altered cell signaling pathways, inhibition of cell growth, preferably cancer cell growth, promotion of cell death, preferably cancer cell death, or the shrinkage of tumors, all of which are observed without severe adverse effects. Slowing, and preferably regressing, the growth of the tumors and also preferably causing complete regression of a cancer is another example of a therapeutic effect. A therapeutic effect may also be an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped.

Severe adverse effects may include those that are life threatening (such as liver failure, abnormal heart rhythms, and certain types of allergic reactions), those that result in persistent or significant disability or hospitalization, or those that cause a birth defect.

As used herein, "pharmaceutically acceptable salts" refer to derivatives of H3B-6527 wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids.

As used herein, "quantifiable" means being able to be measured, calculated or expressed as a quantity or numerical value. A quantifiable plasma concentration is a concentration of H3B-6527 that is able to be detected and measured within the plasma of a human subject after administration. A quantifiable AUC bioavailability is a fraction of H3B-6527 that gains access to the systemic circulation of a human subject that is able to be calculated from analyzing H3B-6527's plasma concentrations in plasma samples taken from a human subject over a set period of time. A quantifiable half-life is a detectable or calculated time period wherein the plasma concentration of H3B-6527 is reduced by 50% along the concentration-time curve of H3B-6527. The methods and materials needed to quantify the aforementioned PK parameters are commonly known to those of ordinary skill in the art. Specific quantification methods are presented within the present application.

As used herein, the term "solvate" means solvent addition forms that contain either stoichiometric or non-stoichiometric amounts of solvent.

Unless specifically stated or obvious from context, as used herein, the term "or" is understood to be inclusive.

An aspect of the present invention provides a dosage form with a therapeutically effective amount of H3B-6527, or a pharmaceutically acceptable salt thereof, and at least one pharmaceutically acceptable carrier or excipient which can be administered to a human subject in need thereof, wherein the therapeutically effective amount achieves a quantifiable plasma concentration after administration.

In an embodiment of the invention, the dosage form is an oral dosage form. In another embodiment of the invention, the dosage form is solid dosage form. In another embodiment of the invention, the dosage form is a solid oral dosage form. In yet another embodiment, the solid oral dosage form may be an immediate release oral solid dosage form. The oral solid dosage form may be in the form of a tablet or capsule. These forms may have multiple phases, including, for example, an internal phase and an external phase.

In one embodiment, the dosage form is substantially free of water. In this context, "substantially" free of water means that the water content of the formulation at the time of packaging is less than 7%, less than 5%, less than 1%, or less than 0.5% of the total weight of the formulation. In one embodiment the amount of water is between 0.1 to 5% (e.g., 0.1-1% or 0.1-0.5%) of the total weight of the formulation. In one embodiment, the amount of water in the formulation of the invention manufactured through a spray-coating process is less than 0.5%.

The at least one pharmaceutically acceptable excipient may be a diluent or inert carrier, a disintegrant, a lubricant, a binder, or a combination thereof. The pharmaceutically acceptable excipient may also include a filler, an antimicrobial agent, an antioxidant, an anti-caking agent, a coating agent, or a mixture thereof.

Exemplary binders may include, but are not limited to corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc.), methyl cellulose, methocel, pre-gelatinized starch (e.g., STARCH 1500® and STARCH 1500 LM®, sold by Colorcon, Ltd.), hydroxypropyl cellulose, hydroxypropyl methyl cellulose, microcrystalline cellulose (FMC Corporation, Marcus Hook, PA, USA), Emdex, Plasdone, or mixtures thereof; fillers, such as talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof.

Exemplary disintegrants may include, but are not limited to: agar-agar, alginic acid, calcium carbonate, microcrystalline cellulose, croscarmellose sodium, crospovidone, polacrilin potassium, sodium starch glycolate (such as Explotab), potato or tapioca starch, other starches, pre-gelatinized starch, clays, other algins, other celluloses, gums (like gellan), low-substituted hydroxypropyl cellulose, ploypl-asdone, or mixtures thereof.

Exemplary lubricants may include, but are not limited to: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, MD USA), a coagulated aerosol of synthetic silica (Deaussa Co., Plano, TX USA), a pyrogenic silicon dioxide (CAB-O-SIL, Cabot Co., Boston, MA USA), or mixtures thereof.

Exemplary coating agents may include, but are not limited to: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, camauba wax, microcrystalline wax, gellan gum, maltodextrin, methacrylates, microcrystalline cellulose and carrageenan or mixtures thereof.

In one embodiment, the dosage form is a solid oral dosage form that may optionally be treated with coating systems (e.g. Opadry® fx film coating system) to be coated with for example Opadry® blue (OY-LS-20921), Opadry® white (YS-2-7063), Opadry® white (YS-1-7040), and black ink (S-1-8 106).

In one embodiment, the oral dosage form is configured into a capsule that possesses an internal phase that comprises a therapeutically effective amount of H3B-6527 or a pharmaceutically acceptable salt thereof, lactose monohydrate, low-substituted hydroxypropyl cellulose, microcrystalline cellulose, hydroxypropylcellulose and colloidal anhydrous silica. The capsule also possesses an external phase comprising magnesium stearate.

In one embodiment, the capsule is hypromellose.

In another embodiment, the capsule is hypromellose and is further comprised of iron oxide red and titanium dioxide.

The pharmaceutically acceptable salt may include conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts may include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

In another embodiment, the dosage form may also comprise one or more active compounds (e.g., H3B-6527 or a salt thereof) in combination with at least one pharmaceutically acceptable excipient or carrier.

Examples of solvates may include, if the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hemihydrate is formed by the combination of one molecule of water with more than one molecule of the substance in which the water retains its molecular state as $H_2O$.

The oral dosage form with a therapeutically effective amount of H3B-6527, or a pharmaceutically acceptable salt thereof, and at least one pharmaceutically acceptable carrier or excipient which can be administered to a human subject in need thereof may achieve a quantifiable plasma concentration from about 2 hr to about 6 hr, from about 3 hr to about 5 hr, from about 3 hr to about 4 hr, or about 4 hr after administration.

A therapeutically effective amount of H3B-6527, or a pharmaceutically acceptable salt thereof, that may be present within the oral dosage form ranges from about 300 mg to about 2000 mg, from about 500 mg to about 1400 mg, from about 600 mg to about 1000 mg, or from about 600 mg to about 700 mg.

The oral dosage form with a therapeutically effective amount of H3B-6527, or a pharmaceutically acceptable salt thereof, and at least one pharmaceutically acceptable carrier or excipient which can be administered to a human subject in need thereof may achieve a maximum quantifiable plasma concentration from about 10 ng/mL to about 900 ng/ml, from about 20 ng/mL to about 800 ng/mL, from about 100 ng/ml to about 400 ng/ml, or from about 150 ng/ml to about 250 ng mL after administration.

The oral dosage form with a therapeutically effective amount of H3B-6527, or a pharmaceutically acceptable salt thereof, and at least one pharmaceutically acceptable carrier or excipient which can be administered to a human subject in need thereof may achieve a half-life from about 2 hr to about 7 hr, from about 2 hr to about 5 hr, from about 3 hr to about 4 hr, or about 4 hr after administration.

The oral dosage form with a therapeutically effective amount of H3B-6527, or a pharmaceutically acceptable salt thereof, and at least one pharmaceutically acceptable carrier or excipient which can be administered to a human subject in need thereof may achieve a quantifiable AUC bioavailability from about 50 ng*hr/mL to about 7,000 ng*hr/mL, from about 150 ng*hr/mL to about 5,700 ng*hr/mL, from about 400 ng*hr/mL to about 700 ng*hr/mL, or from about 500 ng*hr/mL to about 650 ng*hr/mL after administration.

The oral dosage form with a therapeutically effective amount of H3B-6527, or a pharmaceutically acceptable salt thereof, and at least one pharmaceutically acceptable carrier or excipient which can be administered to a human subject in need thereof may be administered orally as a single dose once per day during an 8-day cycle, a 15-day cycle, 20-day cycle, a 21-day cycle, a 22-day cycle, a 23-day cycle, a 24-day cycle, a 25-day cycle, a 26-day cycle, a 27-day cycle, a 28-day cycle or until a therapeutic effect occurs within the subject in need thereof. The dosage form may also be administered in cycles under 20 days.

A. Oral dosage forms comprising from about 300 mg to about 2000 mg of H3B-6527, or a pharmaceutically acceptable salt thereof, and at least one pharmaceutically acceptable excipient.

In some embodiments, an oral dosage form comprises from about 300 mg to about 2,000 mg of H3B-6527, or a pharmaceutically acceptable salt thereof, and at least one pharmaceutically acceptable excipient. In some embodiments the dosage achieves a maximum quantifiable plasma concentration, Cmax (in ng/mL), following administration to a fed subject in need of treatment of from about 100 ng/mL to about 970 ng/mL. In other embodiments the dosage achieves a maximum quantifiable plasma concentration following administration to a fed subject in need of treatment of from about 150 ng/ml to about 850 ng/mL. In other embodiments the dosage achieves a maximum quantifiable plasma concentration following administration to a fed subject in need of treatment of from about 250 ng/ml to about 650 ng/mL. In other embodiments the dosage achieves a maximum quantifiable plasma concentration following administration to a fed subject in need of treatment of from about 350 ng/ml to about 550 ng/mL. In these embodiments the stated Cmax may be achieved in a time between about 2 hours to about 6 hours; about 2 hours to about 4 hours; about 4 hours to about 6 hours; or about 5 hours.

In some embodiment, the oral dosage form comprises from about 300 mg to about 2,000 mg of H3B-6527, or a pharmaceutically acceptable salt thereof, and at least one pharmaceutically acceptable excipient. In some of those embodiments the dosage form achieves a half-life after administration to a fed human subject in need thereof of from about 2.0 hours to about 7.0 hours; a half-life of about 3.0 hours to about 6.0 hours; or a half-life of about 4.0 hours to about 5.0 hours.

In one embodiment, the oral dosage form comprises from about 300 mg to about 2,000 mg of H3B-6527, or a pharmaceutically acceptable salt thereof, and at least one pharmaceutically acceptable excipient. In such an embodiment the dosage may achieve a quantifiable AUC bioavailability (from 0-12 or from 0-24) after administration to a fed human subject in need thereof of from about 500 ng*hr/mL to about 7,000 ng*hr/mL; about 1,000 ng*hr/mL to about 5,070 ng*hr/mL; about 3,000 ng*hr/mL to about 5,070 ng*hr/mL; or about 1,000 ng*hr/mL to about 3,100 ng*hr/mL.

In some embodiments, an oral dosage form comprises from about 300 mg to about 2,000 mg of H3B-6527, or a pharmaceutically acceptable salt thereof, and at least one pharmaceutically acceptable excipient. In some embodiments the dosage achieves a maximum quantifiable plasma concentration, Cmax (in ng/mL), following administration to a fasted subject in need of treatment of from about 10 ng/ml to about 370 ng/ml. In other embodiments the dosage achieves a maximum quantifiable plasma concentration following administration to a fasted subject in need of treatment of from about 20 ng/ml to about 146 ng/mL. In other embodiments the dosage achieves a maximum quantifiable plasma concentration following administration to a fasted subject in need of treatment of from about 100 ng/ml to about 260 ng/mL In these embodiments the stated Cmax may be achieved in a time between about 0.5 hours to about 4 hours; about 0.5 hours to about 2 hours; about 1 hour to about 3 hours; or about 2 hours.

In some embodiment, the oral dosage form comprises from about 300 mg to about 2,000 mg of H3B-6527, or a pharmaceutically acceptable salt thereof, and at least one pharmaceutically acceptable excipient. In some of those embodiments the dosage form achieves a half-life after administration to a fasted human subject in need thereof of from about 1.0 hour to about 6.0 hours; a half-life of about 2.0 hours to about 5.0 hours; or a half-life of about 3.0 hours to about 4.0 hours.

In one embodiment, the oral dosage form comprises from about 300 mg to about 2,000 mg of H3B-6527, or a pharmaceutically acceptable salt thereof, and at least one pharmaceutically acceptable excipient. In such an embodiment the dosage may achieve a quantifiable AUC bioavailability (from 0-12 or from 0-24) after administration to a fasted human subject in need thereof of from about 50 ng*hr/mL to about 1,500 ng*hr/mL; about 400 ng*hr/mL to about 1,500 ng*hr/mL; about 400 ng*hr/mL to about 1,000 ng*hr/mL; or about 400 ng*hr/mL to about 650 ng*hr/mL.

B. Oral dosage forms comprising from about 300 mg to about 700 mg of H3B-6527, or a pharmaceutically acceptable salt thereof, and at least one pharmaceutically acceptable excipient.

In some embodiments, an oral dosage form comprises from about 300 mg to about 700 mg of H3B-6527, or a pharmaceutically acceptable salt thereof, and at least one pharmaceutically acceptable excipient. In some embodiments the dosage achieves a maximum quantifiable plasma concentration, Cmax (in ng/mL), following administration to a fed subject in need of treatment of from about 100 ng/ml to about 270 ng/ml. In other embodiments the dosage achieves a maximum quantifiable plasma concentration following administration to a fed subject in need of treatment of from about 163 ng/ml to about 255 ng/mL. In other embodiments the dosage achieves a maximum quantifiable plasma concentration following administration to a fed subject in need of treatment of from about 150 ng/ml to about 241 ng/mL In these embodiments the stated Cmax may be achieved in a time between about 2 hours to about 4 hours.

In some embodiment, the oral dosage form comprises from about 300 mg to about 700 mg of H3B-6527, or a pharmaceutically acceptable salt thereof, and at least one pharmaceutically acceptable excipient. In some of those embodiments the dosage form achieves a half-life after administration to a fed human subject in need thereof of from about 2.0 hours to about 4.0 hours; or a half-life of about 2.0 hours to about 3.0 hours.

In one embodiment, the oral dosage form comprises from about 300 mg to about 700 mg of H3B-6527, or a pharmaceutically acceptable salt thereof, and at least one pharmaceutically acceptable excipient. In such an embodiment the dosage may achieve a quantifiable AUC bioavailability (from 0-12 or from 0-24) after administration to a fed human subject in need thereof of from about 500 ng*hr/mL to about 1,300 ng*hr/mL; about 500 ng*hr/mL to about 1,000 ng*hr/mL; about 500 ng*hr/mL to about 800 ng*hr/mL; or about 500 ng*hr/mL to about 650 ng*hr/mL.

In some embodiments, an oral dosage form comprises from about 300 mg to about 700 mg of H3B-6527, or a pharmaceutically acceptable salt thereof, and at least one pharmaceutically acceptable excipient. In some embodiments the dosage achieves a maximum quantifiable plasma concentration, Cmax (in ng/mL), following administration to a fasted subject in need of treatment of from about 11 ng/ml to about 255 ng/ml. In other embodiments the dosage achieves a maximum quantifiable plasma concentration following administration to a fasted subject in need of treatment of from about 20 ng/mL to about 125 ng/mL. In other embodiments the dosage achieves a maximum quantifiable plasma concentration following administration to a fasted subject in need of treatment of from about 11 ng/mL to about 200 ng/mL In these embodiments the stated Cmax may be achieved in a time between about 0.5 hours to about 4 hours; about 0.5 hours to about 2 hours; about 1 hour to about 3 hours; or about 2 hours.

In some embodiments, the oral dosage form comprises from about 300 mg to about 700 mg of H3B-6527, or a pharmaceutically acceptable salt thereof, and at least one pharmaceutically acceptable excipient. In some of those embodiments the dosage form achieves a half-life after administration to a fasted human subject in need thereof of from about 1.0 hour to about 5.0 hours; a half-life of about 2.0 hours to about 4.0 hours; or a half-life of about 3.0 hours to about 4.0 hours.

In one embodiment, the oral dosage form comprises from about 300 mg to about 700 mg of H3B-6527, or a pharmaceutically acceptable salt thereof, and at least one pharmaceutically acceptable excipient. In such an embodiment the dosage may achieve a quantifiable AUC bioavailability (from 0-12 or from 0-24) after administration to a fasted human subject in need thereof of from about 50 ng*hr/mL to about 1,200 ng*hr/mL; about 50 ng*hr/mL to about 650 ng*hr/mL; about 50 ng*hr/mL to about 200 ng*hr/mL; or about 400 ng*hr/mL to about 650 ng*hr/mL.

C. Oral dosage forms comprising from about 1000 mg to about 2000 mg of H3B-6527, or a pharmaceutically acceptable salt thereof, and at least one pharmaceutically acceptable excipient.

In some embodiments, an oral dosage form comprises from about 1,000 mg to about 2,000 mg of H3B-6527, or a pharmaceutically acceptable salt thereof, and at least one pharmaceutically acceptable excipient. In some embodiments the dosage achieves a maximum quantifiable plasma concentration, Cmax (in ng/mL), following administration to a fed subject in need of treatment of from about 182 ng/ml to about 965 ng/ml. In other embodiments the dosage achieves a maximum quantifiable plasma concentration following administration to a fed subject in need of treatment of from about 182 ng/ml to about 904 ng/mL. In other embodiments the dosage achieves a maximum quantifiable plasma concentration following administration to a fed subject in need of treatment of from about 650 ng/mL to about 965 ng/mL In these embodiments the stated Cmax may be achieved in a time between about 2 hours to about 6 hours; about 3 hours to about 5 hours; about 2 hours to about 4 hours; or about 4 hours.

In some embodiment, the oral dosage form comprises from about 1,000 mg to about 2,000 mg of H3B-6527, or a pharmaceutically acceptable salt thereof, and at least one pharmaceutically acceptable excipient. In some of those embodiments the dosage form achieves a half-life after administration to a fed human subject in need thereof of from about 3.0 hours to about 7.0 hours; a half-life of about 4.0 hours to 6.0 hours; or a half-life of about 4.0 hours to about 5.0 hours.

In one embodiment, the oral dosage form comprises from about 1,000 mg to about 2,000 mg of H3B-6527, or a pharmaceutically acceptable salt thereof, and at least one pharmaceutically acceptable excipient. In such an embodiment the dosage may achieve a quantifiable AUC bioavailability (from 0-12 or from 0-24) after administration to a fed human subject in need thereof of from about 800 ng*hr/mL to about 7,000 ng*hr/mL; about 1,000 ng*hr/mL to about 6,000 ng*hr/mL; about 3,000 ng*hr/mL to about 6,000 ng*hr/mL; or about 5,000 ng*hr/mL to about 7,000 ng*hr/mL.

In some embodiments, an oral dosage form comprises from about 1,000 mg to about 2,000 mg of H3B-6527, or a pharmaceutically acceptable salt thereof, and at least one pharmaceutically acceptable excipient. In some embodiments the dosage achieves a maximum quantifiable plasma concentration, Cmax (in ng/mL), following administration to a fasted subject in need of treatment of from about 135 ng/ml to about 365 ng/ml. In other embodiments the dosage achieves a maximum quantifiable plasma concentration following administration to a fasted subject in need of treatment of from about 130 ng/ml to about 150 ng/mL. In other embodiments the dosage achieves a maximum quantifiable plasma concentration following administration to a fasted subject in need of treatment of from about 195 ng/ml to about 365 ng/mL In these embodiments the stated Cmax may be achieved in a time between about 1 hour to about 2 hours.

In some embodiment, the oral dosage form comprises from about 1,000 mg to about 2,000 mg of H3B-6527, or a pharmaceutically acceptable salt thereof, and at least one pharmaceutically acceptable excipient. In some of those embodiments the dosage form achieves a half-life after administration to a fasted human subject in need thereof of from about 4.0 hour to about 5.0 hours.

In one embodiment, the oral dosage form comprises from about 1,000 mg to about 2,000 mg of H3B-6527, or a pharmaceutically acceptable salt thereof, and at least one pharmaceutically acceptable excipient. In such an embodiment the dosage may achieve a quantifiable AUC bioavailability (from 0-12 or from 0-24) after administration to a fasted human subject in need thereof of from about 400 ng*hr/mL to about 1,500 ng*hr/mL; about 400 ng*hr/mL to about 1,000 ng*hr/mL; about 400 ng*hr/mL to about 650 ng*hr/mL; or about 600 ng*hr/mL to about 1,500 ng*hr/mL.

EXAMPLES

Example 1: Capsule Formulation 50 mg, 100 mg and 200 mg strength capsules were formulated according to the following table:

TABLE 1

Components and Compositions of Formula I Capsules, 50 mg, 100 mg and 200 mg

| Components[a] | Composition 50 mg Amount (mg) | 100 mg | 200 mg | Function | Specification |
|---|---|---|---|---|---|
| Internal Phase (Granules) | | | | | |
| H3B-6527 drug substance[b] | 50.0 | 100.0 | 200.0 | Active ingredient | In-house |
| Lactose monohydrate[c] | 4.32 | 8.64 | 17.28 | Diluent | JP, NF, Ph. Eur. |
| Calcium carbonate | 37.8 | 75.6 | 151.2 | Diluent | JP, USP, Ph. Eur. |
| Copovidone | 11.1 | 22.2 | 44.4 | Binder | JPE, NF, Ph. Eur. |
| Low-substituted hydroxypropyl cellulose | 5.56 | 11.12 | 22.24 | Disintegrant | JP, NF |
| Colloidal silicon dioxide | 1.31 | 2.22 | 4.44 | Glidant | JP, NF, Ph. Eur, |
| Magnesium stearate | 1.11 | 2.22 | 4.44 | Lubricant | JP, NF, Ph. Eur. |
| Total of Capsule Content Capsule | 111.0 | 222.0 | 444.0 | — | — |
| HPMC capsule[d] | 38.0 | 60.0 | 90.0 | Capsule shell | JP |
| Total Capsule Weight | 149.0 | 282.0 | 534.0 | — | — |

HPMC = Hypromellose,
NF = National Formulary (US),
Ph. Eur. = European Pharmacopoeia,
USP = United States Pharmacopeia,
JP = Japanese Pharmacopoeia,
JPE = Japanese Pharmaceutical Excipients
[a]Names of components (except for H3B-6527 drug substance and HPMC capsule) are written according to USP or NF.
[b]The quantity of H3B-6527 drug substance is adjusted as per potency adjustment factor, a derived value for the assay value.
[c]Compounding amount of lactose monohydrate is adjusted depending on the quantity of H3B-6527 drug substance in order to maintain constant weight of granules.
[d]Components and composition of the HPMC capsule shell are provided in Table 2.

TABLE 2

Components and Composition of HPMC Capsule Shell

| Component | Specification | Composition (Pow/WF) |
|---|---|---|
| Iron oxide red | JPE, NF, EC Regulation (E172) | 1.1% |
| Titanium dioxide | JP, USP, Ph. Eur | 0.6% |
| Hypromellose | JP, USP, Ph. Eur. | q.s. to 100% |

IPE = Japanese Phannaceutical Excipients,
NF = National Formulary (US),
JP = Japanese Pharmacopoeia,
USP = United States Pharmacopeia,
EC Regulation = European Commission Regulation,
Ph. Eur. = European Pharmacopoeia,
q.s. = quantum sufficit
E172 is an European standard for iron oxide and hydroxides

TABLE 3

| Specification of Excipients | |
|---|---|
| Component | Specification |
| Lactose monohydrate | JP, NF, Ph. Eur. |
| Calcium carbonate | JP, USP, Ph. Eur. |
| Copovidone | JPE, NF, Ph. Eur. |
| Low-substituted hydroxypropyl cellulose | JP, NF |
| Colloidal silicon dioxide | JP. NF, Ph. Eur. |
| Magnesium stearate | JP. NF, Ph. Eur. |
| HPMC capsule | JP |
| Iron oxide red | JPE, NF, BC Regulation (E172) |
| Titanium dioxide | JP, USP, Ph. Eur. |
| Hypromellose | JP, USP, Ph. Eur. |

HPMC = Hypromellose,
NF = National Formulary (US),
Ph. Eur. = European Pharmacopoeia,
USP = United States Phannacopeia,
JP = Japanese Pharmacopoeia,
JPE = Japanese Pharmaceutical Excipients, EC
Regulation = European Commission Regulation,
E172 is a European standard for iron oxide and hydroxides Capsules are formed as follows: H3B-6527 drug substance, lactose monohydrate, calcium carbonate, copovidone, low-substituted hydroxypropyl cellulose and colloidal silicon dioxide are mixed into a high shear mixer to form a first mixture. Magnesium stearate is then mixed with the first mixture using a high shear mixer to form a final mixture. The final mixture undergoes granulation by compressing it into ribbons using a roller compactor and then sizing by passing the resulting ribbons through a screen. The sized granules are filled into HPMC capsules using an encapsulator. Overweight and underweight capsules are eliminated using a checkweigher.

Example 2: Pharmacokinetic (PK) Measurements of Capsules in Patients

A description of the first in human clinical trial for H3B-6527 can be found at the ClinicalTrials.gov by searching for trial identifier NCT02834780. In summary, the trial included a study population having the following characteristics: Adult patients ≥18 years old with advanced HCC or ICC; Progression after at least one prior therapy; ECOG score of 0 or 1; Well compensated liver function; FGF19-positive (dose expansion phase only); Excluded if patients have significant active infections [except hepatitis B virus (HBV) and hepatitis C virus (HCV)], gastric or esophageal varices, or previous FGF19-FGFR4 targeted therapy.

Blood samples are collected at the planned time points from each patient and centrifuged. The plasma portion of each sample is then transferred to a K2EDTA tube, which is then shipped to a bioanalytical lab for concentration measurement using LC-MS/MS. The concentration data are then analyzed using Phoenix® WinNonlin software to obtain PK parameters. The obtained PK parameters are further summarized using analytical software.

Drug Administration and Dosage for Dose Escalation: H3B-6527 was administered orally QD or BID on a 21-day cycle. Dose escalation followed a standard 3+3 cohort design with the dose cohorts of 300, 600, 1000, and 1400 mg QD fasting or 500 and 700 mg BID fed. Patients in dose escalation phase were treated regardless of FGF19 status. Response determined by RECIST 1.1/modified RECIST every 6 weeks Pharmacokinetics (PK) Results:

H3B-6527 was rapidly absorbed with a median plasma $t_{max}$ of ~1 to 3 h (fasted)

H3B-6527 plasma levels increased with dose from 300 to 1000 mg QD and plateaued (fasted) (FIG. 1)

H3B-6527 showed a mean terminal half-life of ~4 to 5 h, following administration of 1000 mg (fasted)

FIG. 1. Mean Plasma-concentration over Time Profile for H3B-6527 (Cycle 1, Day 8). Preliminary PK analysis indicates that H3B-6527 plasma exposure increased with dose up to 1000 mg QD in fasted state. A higher minimal plasma concentration was maintained on the BID schedule.

On the once daily fasted schedule:

2 (7.4%) patients with HCC achieved partial responses 20 (74.1%) had stable disease

TABLE 4

Tumor Response in Patients with HCC

| | 300 mg QD Fasted (N = 3) n (%) | 600 mg QD Fasted (N = 3) n (%) | 1000 mg QD Fasted (N = 7) n (%) | 1400 mg QD Fasted (N = 4) n (%) | Expansion 1000 mg QD Fasted (N = 10) n (%) | Total (N = 27) n (%) |
|---|---|---|---|---|---|---|
| Best Overall Response, N (%) | | | | | | |
| Complete Response (CR) | 0 (0.0) | 0 (0.0) | 0 (0.0) | 0 (0.0) | 0 (0.0) | 0 (0.0) |
| Partial Response (PR) | 0 (0.0) | 0 (0.0) | 1 (14.3) | 1 (25.0) | 0 (0.0) | 2 (7.4) |
| Stable Disease (SD) | 3 (100.0) | 2 (66.7) | 6 (85.7) | 3 (75.0) | 6 (60.0) | 20 (74.1) |
| Progressive Disease (PD) | 0 (0.0) | 1 (33.3) | 0 (0.0) | 0 (0.0) | 1 (10.0) | 2 (7.4) |
| Not Evaluable | 0 (0.0) | 0 (0.0) | 0 (0.0) | 0 (0.0) | 0 (0.0) | 0 (0.0) |
| Unknown | 0 (0.0) | 0 (0.0) | 0 (0.0) | 0 (0.0) | 3 (30.0) | 3 (11.1) |
| Objective Response Rate (CR + PR), n (%) | 0 (0.0) | 0 (0.0) | 1 (14.3) | 1 (25.0) | 0 (0.0) | 2 (7.4) |
| Clinical Benefit Rate (CBR)(CR + PR + Durable SD), n (%)* | 1 (33.3) | 2 (66.7) | 5 (71.4) | 3 (75.0) | 2 (20.0) | 13 (48.1) |

*Durable SD = stable disease ≥ 17 weeks

Figure 2:
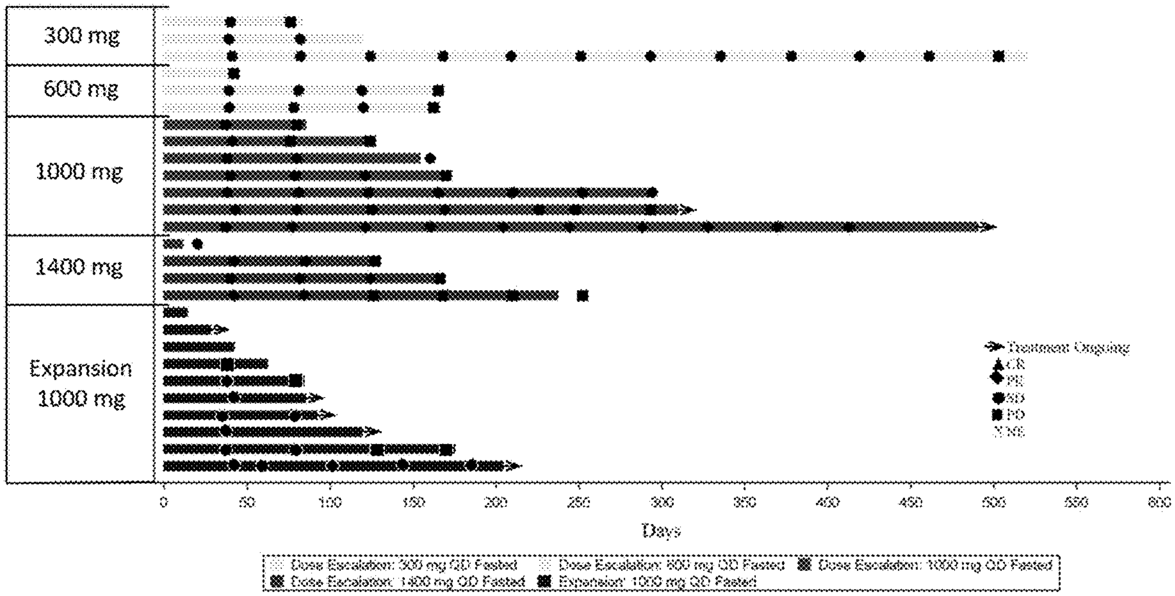
FIG. 2 shows tumor response and duration of H3B-6527 treatment as reported more fully in Example 2, below. The duration of treatment with 300 to 1400 mg QD of H3B-6527 in HCC patients in the full analysis set is shown. CR=complete response, PR=partial response, SD=stable disease, PD=progressive disease, and NE=not evaluated.

FIG. 2. Tumor Response and Duration of H3B-6527 Treatment. The duration of treatment with 300 to 1400 mg QD of H3B-6527 in HCC patients in the full analysis set is shown. CR-complete response, PR=partial response, SD=stable disease, PD=progressive disease, and NE=not evaluated.

Figure 3:
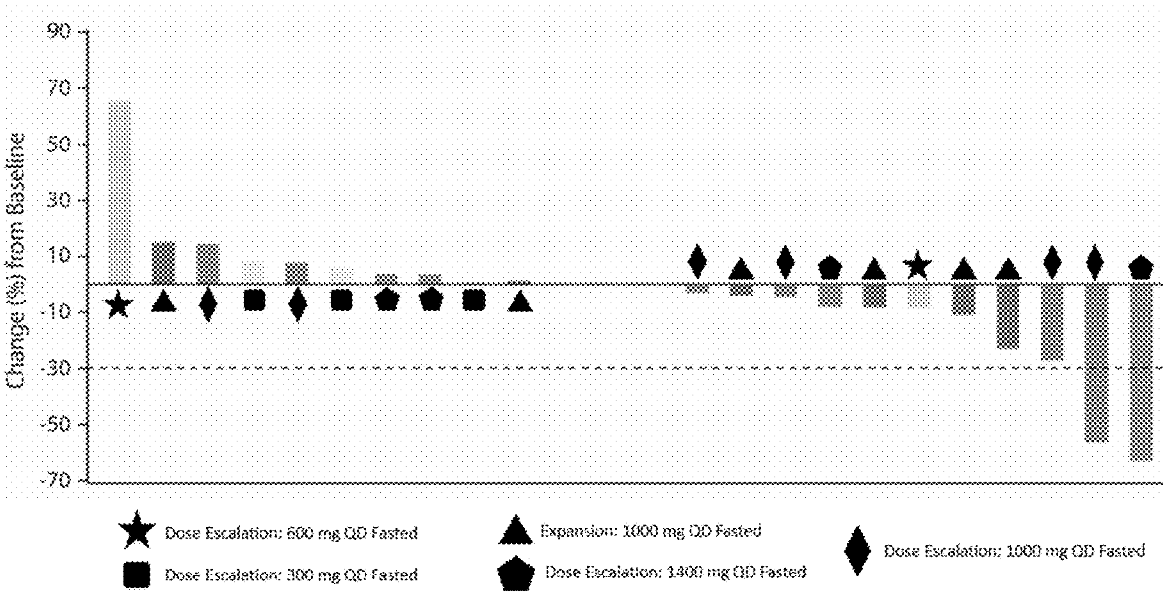
FIG. 3 shows percentage change in sum of diameters of target lesions as reported in Example 2.

FIG. 3 shows percentage change in sum of diameters of target lesions as measured for this Example.

Example 3: Further PK Analysis

Further collection and collation of the PK results of the trial of Example 2 at a later point in time are reflected in the following Table 5:

TABLE 5

| regimen | dose(mg) | n | Tmax(hr) | Cmax(ng/mL) | AUC(ng · mg/mL) | Half-life(hr) | Fed | Day |
|---|---|---|---|---|---|---|---|---|
| QD | 300 | 3 | 2 (2-4) | 20 (64.1) | 73 (60.6) | 1.4 (25.8) | 0 | 1 |
| QD | 300 | 3 | 4 (2.07-4) | 11 (90.6) | 53 (50.7) | 1.2 (18.4) | 0 | 8 |
| BID | 500 | 3 | 2.75 (2.12-4.57) | 124 (159.1) | 470 (134.5) | 1.9 (6) | 0 | 1 |
| BID | 500 | 4 | 3.05 (0-4.17) | 253 (37.4) | 1195 (37.9) | 1.8 (17.1) | 0 | 8 |
| BID | 500 | 11 | 4.02 (0.57-10) | 255 (251.6) | 769 (199.1) | 2.1 (43.4) | 1 | 1 |
| BID | 500 | 34 | 4 (0-10) | 262 (166) | 1075 (162.5) | 2.3 (30.4) | 1 | 8 |
| QD | 600 | 3 | 1 (0.5-2) | 74 (1389.4) | 175 (1851.4) | 2.4 (42) | 0 | 1 |
| QD | 600 | 3 | 0.52 (0.5-2) | 194 (45.6) | 636 (39.4) | 4.8 (12.8) | 0 | 8 |
| QD | 600 | 3 | 4 (2.05-4.07) | 241 (289.5) | 1282 (494.5) | 3.7 (6.1) | 1 | 1 |
| QD | 600 | 4 | 4.52 (0.53-6) | 100 (5300.4) | 502 (2960.5) | 3.2 (16.1) | 1 | 8 |
| BID | 700 | 5 | 2.02 (0.5-6.12) | 163 (303.2) | 590 (479.8) | 2.1 (46.3) | 1 | 1 |
| BID | 700 | 5 | 4.12 (0.5-10) | 167 (202.7) | 640 (358.8) | 2.2 (36.3) | 1 | 8 |
| QD | 1000 | 10 | 2.01 (0.533-8.12) | 146 (1018.5) | 602 (821.8) | 4.5 (42.7) | 0 | 1 |
| QD | 1000 | 30 | 2.02 (0.33-24) | 197 (319.4) | 912 (385) | 4.5 (39) | 0 | 8 |
| QD | 1000 | 4 | 5.05 (1-6) | 188 (277.3) | 1100 (427) | 4 (45.7) | 1 | 1 |
| QD | 1000 | 3 | 4.08 (2-4.5) | 199 (1218.9) | 865 (688.5) | 4.2 (79.5) | 1 | 8 |
| QD | 1400 | 7 | 1 (0.63-4.15) | 136 (429.4) | 400 (188) | 5.3 (38.4) | 0 | 1 |
| QD | 1400 | 7 | 2.1 (1.75-5.12) | 362 (898.5) | 1449 (407.1) | 4.9 (66.1) | 0 | 8 |
| QD | 1400 | 4 | 5 (2-8) | 904 (34.2) | 5669 (98.7) | 4.1 (13.2) | 1 | 1 |
| QD | 1400 | 4 | 5.86 (2-6.22) | 827 (40.6) | 5450 (75) | 4.4 (3.7) | 1 | 8 |
| QD | 2000 | 6 | 2 (1-6) | 525 (89.2) | 3034 (74.2) | 5.5 (32.5) | 1 | 1 |
| QD | 2000 | 6 | 2.5 (1-6) | 451 (98.2) | 1922 (176.4) | 5.7 (60.9) | 1 | 8 |

Note:
median (min-max) for Tmax;
geometric mean (CV %) for Cmax, AUC, and half-life.
Fed = 0 means "fasted," and Fed = 1 means "fed."
n is the number of patients.
QD refers to dosage administered once/day;
BID refers to dosage administered twice/day.

Example 4: Further PK Analysis

The results of further analysis of the PK data of the trial of Example 2 with the actual date and time of the dose administration and PK sampling after QC, an update from the results of a preliminary analysis with the nominal (i.e. planned) dosing/PK sampling date/time presented in Example 3, are reflected in the following Table 6. In this example the number of patients from which each PK parameter was calculated is shown, rather than the total number of patients receiving a particular dose and regimen as in Table 5.

TABLE 6

| regimen | dose(mg) | Tmax(hr); n | Cmax(ng/mL); n | AUC(ng · h/mL); n | Half-life(h); n | Fed | Day |
|---|---|---|---|---|---|---|---|
| QD | 300 | 2 (2.00-4.00); 3 | 20.3 (64.1); 3 | 72.7 (60.0); 3 | 2.52 (134.6); 3 | 0 | 1 |
| QD | 300 | 4 (2.07-4.00); 3 | 10.8 (90.6); 3 | 53.0 (51.4); 3 | 3.55 (526.0); 3 | 0 | 8 |
| BID | 500 | 2.12(2.00-4.57); 3 | 124 (159.1); 3 | 292 (98.2); 2 | 2.41 (28.2); 2 | 0 | 1 |
| BID | 500 | 4 (2.10-4.17); 3 | 251 (46.5); 3 | 1106 (36.9); 3 | 2.96 (47.4); 3 | 0 | 8 |
| BID | 500 | 4.02 (0.57-10.00); 10 | 255 (251.6); 10 | 768 (199.8); 10 | 2.33 (49.1); 7 | 1 | 1 |
| BID | 500 | 4 (0.00-10.00); 45 | 211 (237.2); 45 | 814 (229.1); 43 | 2.99 (82.4); 32 | 1 | 8 |
| QD | 600 | 1 (0.50-2.00); 3 | 74.5 (1389.4); 3 | 175 (1867); 3 | 7.19 (606.2); 3 | 0 | 1 |
| QD | 600 | 0.52 (0.50-2.00); 3 | 194 (45.6); 3 | 636 (39.4); 3 | 7.32 (86.0); 3 | 0 | 8 |
| QD | 600 | 4 (1.00-4.07); 3 | 395 (133.7); 3 | 1631 (271.9); 3 | 3.72 (6.0); 3 | 1 | 1 |

TABLE 6-continued

| regimen | dose(mg) | Tmax(hr); n | Cmax(ng/mL); n | AUC(ng · h/mL); n | Half-life(h); n | Fed | Day |
|---|---|---|---|---|---|---|---|
| QD | 600 | 4.52 (0.53-6.00); 4 | 99.6 (5300.4); 4 | 501 (2978.0); 4 | 5.88 (195.7); 4 | 1 | 8 |
| BID | 700 | 2.02 (0.50-6.12); 5 | 163 (303.2); 5 | 591 (475.4); 5 | 2.13 (46.4); 3 | 1 | 1 |
| BID | 700 | 4.12 (0.50-10.00); 5 | 167 (202.7); 5 | 639 (360.6); 5 | 2.18 (36.4); 3 | 1 | 8 |
| QD | 1000 | 2.02 (1.00-8.12); 9 | 225 (470.2); 9 | 854 (523.0); 9 | 4.48 (42.7); 8 | 0 | 1 |
| QD | 1000 | 2 (0.33-10.00); 32 | 187 (339.1); 32 | 839 (420); 31 | 4.84 (54.9); 30 | 0 | 8 |
| QD | 1000 | 6(4.10-6.00); 3 | 182 (494.6); 3 | 1115 (909.7); 3 | 3.94 (57.1); 3 | 1 | 1 |
| QD | 1000 | 2 (1.00-4.33); 7 | 177 (370.3); 7 | 796 (342.0); 7 | 6.16 (106.7); 7 | 1 | 8 |
| QD | 1400 | 1 (0.63-4.15); 7 | 136 (429.4); 7 | 400 (186.9); 7 | 6.13 (52.6); 7 | 0 | 1 |
| QD | 1400 | 2.1(1.00-4.13); 7 | 362 (898.5); 7 | 1264 (760.6); 7 | 4.56 (63.3); 7 | 0 | 8 |
| QD | 1400 | 5 (2.00-8.00); 4 | 904 (34.2); 4 | 5669 (98.6); 4 | 4.13 (13.2); 2 | 1 | 1 |
| QD | 1400 | 5.86 (2.00-6.22); 4 | 827 (40.6); 4 | 5449 (75.0); 4 | 4.75 (12.0); 3 | 1 | 8 |
| QD | 2000 | 2.1 (1.00-4.92); 7 | 540 (79.9); 7 | 2947 (61.9); 7 | 4.14 (24.0); 6 | 1 | 1 |
| QD | 2000 | 4 (1.00-8.42); 7 | 502 (95.2); 7 | 2577 (180.0); 5 | 4.98 (58.2); 5 | 1 | 8 |

Note:
median (min-max) for Tmax;
geometric mean (CV %) for Cmax, AUC, and half-life.
Fed = 0 means "fasted," and Fed = 1 means "fed."
n is the number of patients.
QD refers to dosage administered once/day;
BID refers to dosage administered twice/day.

Figure 4:
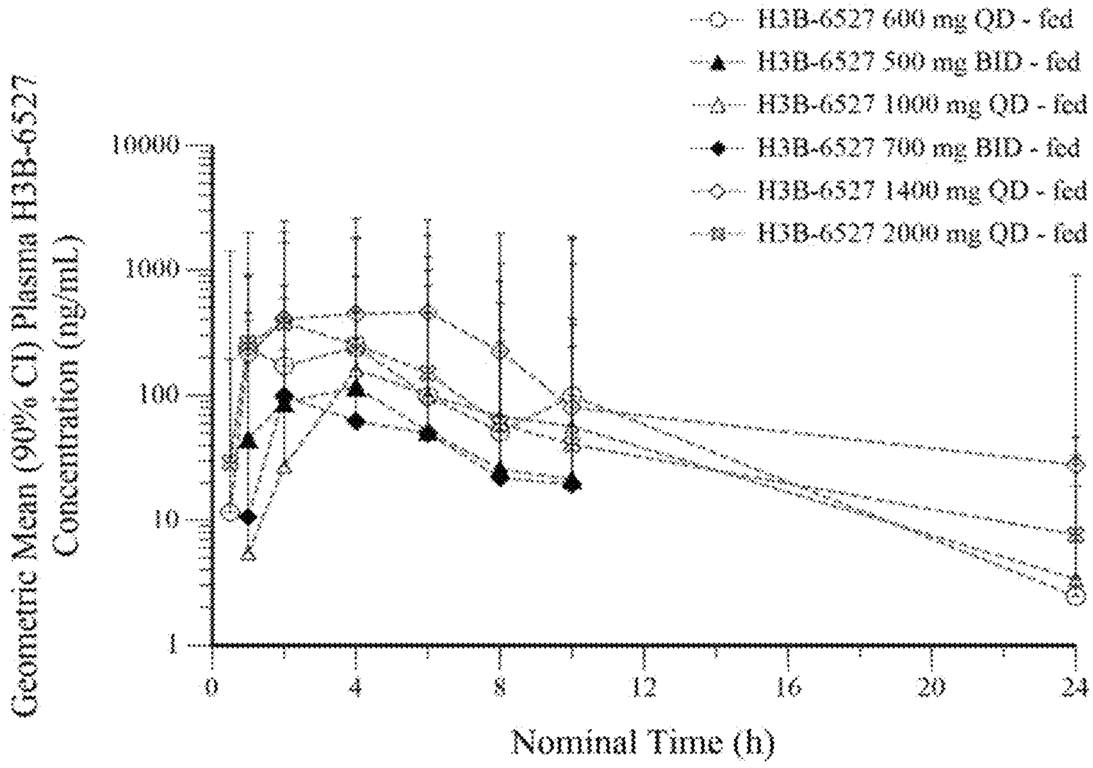
FIG. 4 shows geometric mean plasma concentration over time profile for H3B-6527 as further reported in Example 4. With large variability and limited data, H3B-6527 exposure in plasma appeared to be similar across the doses from 500 mg to 2000 mg administered with food.

FIG. 4 shows geometric mean plasma concentration over time profile for H3B-6527 as further reported in this Example 4.

Example 5: Efficacy

Efficacy was considered following further progress of the trial in Example 2. Among 90 patients with hepatocellular carcinoma ("HCC") treated with H3B-6527, confirmed overall response rate (ORR) was 8.3% in the QD group and 0% in the BID group. The clinical benefit rate (complete response+partial response+durable stable disease) was 52% for the QD group and 38% for the BID group. Moreover, among all HCC patients, median progression-free survival (PFS) was 4.1 months for the QD group and 3.4 months for the BID group; median overall survival (OS) was 11.1 months in the QD group and 8.0 months in the BID group.

Among the 55 HCC patients with ≥2 prior lines of therapy, confirmed ORR was 12.5% in the QD group and 0% in the BID group. The clinical benefit rate was 45.8% in the QD group and 25.8% in the BID group. Moreover, among HCC patients with ≥2 prior lines of therapy, median PFS was 4.1 months for the QD group and 2.8 months for the BID group; median OS was 10.6 months and 7.3 months in the QD and BID groups, respectively.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An oral dosage form comprising:

i) an internal phase including an amount of a compound given by Formula I or a pharmaceutically acceptable salt thereof, wherein said compound of Formula I is N-(2-((6-(3-(2,6-dichloro-3,5-dimethoxyphenyl)-1-methylureido)pyrimidin-4-yl)amino)-5-(4-ethylpiperazin-1-yl)phenyl) acrylamide represented by the structure:

(Formula I)

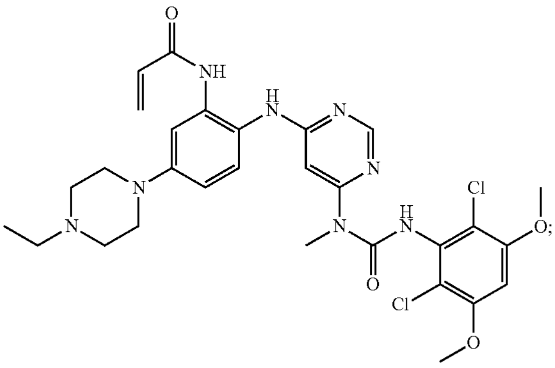

;

lactose monohydrate, calcium carbonate, copovidone, low-substituted hydroxypropyl cellulose, colloidal silicon dioxide and magnesium stearate, and ii) an external phase that encapsulates the internal phase, wherein the internal phase includes:

50 mg of the compound given by Formula I or a pharmaceutically acceptable salt thereof;

4.32 mg of the lactose monohydrate;

37.8 mg of the calcium carbonate;

11.1 mg of the copovidone;

5.56 mg of the low-substituted hydroxypropyl cellulose;

1.11 mg of the colloidal silicon dioxide; and 1.11 mg of the magnesium stearate.

2. An oral dosage form comprising:

i) an internal phase including an amount of a compound given by Formula I or a pharmaceutically acceptable salt thereof, wherein said compound of Formula I is N-(2-((6-(3-(2,6-dichloro-3,5-dimethoxyphenyl)-1-methylureido)pyrimidin-4-yl)amino)-5-(4-ethylpiperazin-1-yl)phenyl) acrylamide represented by the structure:

(Formula I)

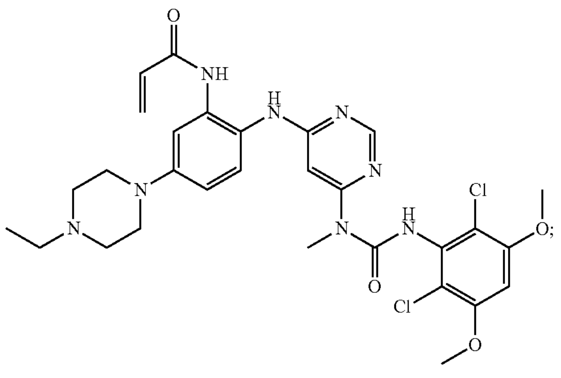

lactose monohydrate, calcium carbonate, copovidone, low-substituted hydroxypropyl cellulose, colloidal silicon dioxide and magnesium stearate, and ii) an external phase that encapsulates the internal phase, wherein the internal phase includes:

100 mg of the compound given by Formula I or a pharmaceutically acceptable salt thereof;

8.64 mg of the lactose monohydrate;

75.6 mg of the calcium carbonate;

22.2 mg of the copovidone;

11.12 mg of the low-substituted hydroxypropyl cellulose;

2.22 mg of the colloidal silicon dioxide; and 2.22 mg of the magnesium stearate.

3. An oral dosage form comprising:

i) an internal phase including an amount of a compound given by Formula I or a pharmaceutically acceptable salt thereof, wherein said compound of Formula I is N-(2-((6-(3-(2,6-dichloro-3,5-dimethoxyphenyl)-1-methylureido)pyrimidin-4-yl)amino)-5-(4-ethylpiperazin-1-yl)phenyl) acrylamide represented by the structure:

(Formula I)

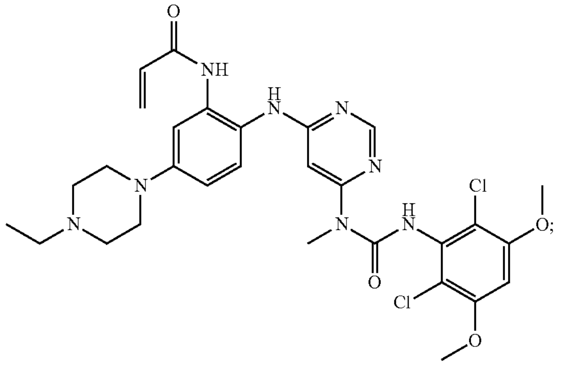

lactose monohydrate, calcium carbonate, copovidone, low-substituted hydroxypropyl cellulose, colloidal silicon dioxide and magnesium stearate, and ii) an external phase that encapsulates the internal phase, wherein the internal phase includes:

200 mg of the compound given by Formula I or a pharmaceutically acceptable salt thereof;

17.28 mg of the lactose monohydrate;

151.2 mg of the calcium carbonate;

44.4 mg of the copovidone;

22.24 mg of the low-substituted hydroxypropyl cellulose;

4.44 mg of the colloidal silicon dioxide; and 4.44 mg of the magnesium stearate.

4. The oral dosage form of claim 3, wherein the external phase includes magnesium stearate.

5. The oral dosage form of claim 3, wherein the oral dosage form is a capsule.

6. The oral dosage form of claim 5, wherein the external phase is a capsule shell including iron oxide red, titanium dioxide and hypromellose.

7. The oral dosage form of claim 6, wherein the capsule shell comprises by total weight of the capsule shell: 1.1 wt % of the iron oxide red, 0.6 wt % of the titanium dioxide, and 98.3 wt % of the hypromellose.

8. The oral dosage form of claim 3, wherein the compound given by Formula I or a pharmaceutically acceptable salt thereof is a hydrochloride salt.

9. A method of treating cancer in a human subject comprising administering to said subject the oral dosage form of claim 3.

10. The method according to claim 9, wherein said cancer is hepatocellular carcinoma.

11. The method according to claim 10, wherein said cancer expresses or overexpresses FGFR4 or FGF19.

12. The method according to claim 9, wherein said oral dosage form is administered to the human subject in a fasted state.

13. The method according to claim 9, wherein said oral dosage form is administered to the human subject in a fed state.

14. The method according to claim 9, wherein the oral dosage form is administered to the subject in a total equivalent amount of about 300 mg to about 1400 mg per day of the compound given by Formula I.

15. The method according to claim 9, wherein the oral dosage form is administered to the subject in a total equivalent amount of about 500 mg to about 1000 mg per day of the compound given by Formula I.

16. The method according to claim 9, wherein administration of the oral dosage form achieves a mean $C_{max}$ of the compound given by Formula I of about 10 ng/ml to about 1000 ng/ml in the subject.

17. The method according to claim 16, wherein the dosage form achieves a mean $t_{max}$ of said mean $C_{max}$ in about 0.5 hours to about 8 hours after administration to the human subject.

18. The method according to claim 9, wherein administration of the oral dosage form achieves a mean $AUC_{0-24}$ of the compound given by Formula I of about 50 h*ng/ml to about 5700 h*ng/mL.

19. The method according to claim 9, wherein administration of the oral dosage form achieves a mean $t_{1/2}$ of the compound given by Formula I of about 1 hour to about 6 hours.

20. The method according to claim 9, wherein administration of the oral dosage form achieves a mean $AUC_{0-12}$ of the compound given by Formula I of about 400 h*ng/ml to about 1200 h*ng/mL.

21. The oral dosage form of claim 1, wherein the compound given by Formula I or a pharmaceutically acceptable salt thereof is a free base form of Formula I.

22. The oral dosage form of claim 2, wherein the compound given by Formula I or a pharmaceutically acceptable salt thereof is a free base form of Formula I.

23. The oral dosage form of claim 3, wherein the compound given by Formula I or a pharmaceutically acceptable salt thereof is a free base form of Formula I.

24. The method of claim 9, wherein the compound given by Formula I or a pharmaceutically acceptable salt thereof is a free base form of Formula I.

25. A method of treating hepatocellular carcinoma in a human subject comprising administering to said subject the oral dosage form of claim 1.

26. The method of claim 25, wherein the compound given by Formula I or a pharmaceutically acceptable salt thereof is a free base form of Formula I.

27. A method of treating hepatocellular carcinoma in a human subject comprising administering to said subject the oral dosage form of claim 2.

28. The method of claim 27, wherein the compound given by Formula I or a pharmaceutically acceptable salt thereof is a free base form of Formula I.

29. The oral dosage form of claim 2, wherein the oral dosage form is a capsule, and wherein the external phase is a capsule shell including hypromellose.

* * * * *